(12) United States Patent
Lamraoui et al.

(10) Patent No.: US 12,727,984 B2
(45) Date of Patent: Sep. 8, 2026

(54) IMPLANTABLE MEDICAL DEVICE

(71) Applicant: UROMEMS, Grenoble (FR)

(72) Inventors: Hamid Lamraoui, Vaulnaveys le Haut (FR); Thierry Ho, Saint Egreve (FR)

(73) Assignee: UROMEMS, Grenoble (FR)

( * ) Notice: Subject to any disclaimer, the term of this patent is extended or adjusted under 35 U.S.C. 154(b) by 705 days.

(21) Appl. No.: 18/035,536

(22) PCT Filed: Dec. 9, 2021

(86) PCT No.: PCT/FR2021/052248
§ 371 (c)(1),
(2) Date: May 5, 2023

(87) PCT Pub. No.: WO2022/123180
PCT Pub. Date: Jun. 16, 2022

(65) Prior Publication Data

US 2023/0390044 A1 Dec. 7, 2023

(30) Foreign Application Priority Data

Dec. 10, 2020 (FR) ...................................... 2013008

(51) Int. Cl.
*A61F 2/00* (2006.01)
*A61F 2/48* (2006.01)
(Continued)

(52) U.S. Cl.
CPC .............. *A61F 2/004* (2013.01); *A61F 2/484* (2021.08); *G01C 5/06* (2013.01); *G01L 1/04* (2013.01);
(Continued)

(58) Field of Classification Search
CPC .. A61F 2/004; A61F 2/484; A61F 2250/0003; A61F 2250/0013;
(Continued)

(56) References Cited

U.S. PATENT DOCUMENTS 10,252,037 B2 4/2019 Degen
10,350,044 B2 7/2019 Lamraoui
(Continued)

FOREIGN PATENT DOCUMENTS

CN 103492015 A 1/2014
CN 107106282 A 8/2017
WO 2016083428 A1 6/2016

OTHER PUBLICATIONS

French Search Report in related French Application No. FR 8895999, mailed Aug. 17, 2021.

(Continued)

*Primary Examiner* — Sunita Reddy
(74) *Attorney, Agent, or Firm* — Thomas | Horstemeyer, LLP

(57) ABSTRACT

The invention relates to a medical device comprising: —a sealed casing (1), suited to being implanted in the body of a human or animal patient, —an inflatable element (3), —a fluidic circuit comprising a fluid reservoir (5) having a variable fluid volume and arranged inside the casing with a tube (2) between the reservoir and the inflatable element, —an actuator arranged inside the casing to selectively vary the volume of fluid in the reservoir, —a control unit (100) configured to control the actuator, —at least one sensor suited to measuring an absolute gauge pressure of the fluid in the fluidic circuit, a force exerted on the reservoir, a gas pressure inside the casing, an atmospheric pressure or a value relating to an altitude of the patient, the control unit (100) being configured so as: —on the basis of a measurement from said sensor while the actuator is inactive, to detect a differential between a value relating to an altitude of the patient and a reference value, and —as a function of said differential, to determine the command to be issued to the
(Continued)

actuator so as to control the pressure of fluid in the fluidic circuit.

21 Claims, 2 Drawing Sheets

(51) Int. Cl.
*G01C 5/06* (2006.01)
*G01L 1/04* (2006.01)

(52) U.S. Cl.
CPC ................ *A61F 2250/0003* (2013.01); *A61F 2250/0013* (2013.01)

(58) Field of Classification Search
CPC ...... A61F 2250/0001; A61F 2250/0002; A61F 2250/001; A61F 2250/0004; G01C 5/06; G01L 1/04
USPC ...................................................... 600/29–32
See application file for complete search history.

(56) References Cited

U.S. PATENT DOCUMENTS

2009/0204132 A1* 8/2009 Ortiz ...................... F04B 43/09 606/157
2011/0208229 A1 8/2011 Snow
2012/0157759 A1* 6/2012 Wirbisky ................ A61F 2/004 600/31
2015/0374288 A1* 12/2015 Lamraoui ............ A61B 5/1116 600/31
2016/0000583 A1 1/2016 Ballas
2016/0123835 A1* 5/2016 Lamraoui .............. A61F 5/005 606/157
2017/0325926 A1 11/2017 Lamraoui

OTHER PUBLICATIONS

International Search Report in related PCT Application No. PCT/FR2021/052248, Apr. 4, 2022.

* cited by examiner

IMPLANTABLE MEDICAL DEVICE

CROSS REFERENCE TO RELATED APPLICATIONS

This application is the 35 U.S.C. § 371 national stage application of PCT Application No. PCT/FR2021/052248, filed Dec. 9, 2021, which application claims the benefit of French Application No. FR 2013008 filed Dec. 10, 2020, both of which are hereby incorporated by reference herein in their entireties.

TECHNICAL FIELD

The invention relates to an implantable medical device comprising a fluid circuit, for selectively closing an anatomical conduit.

PRIOR ART

Medical devices exist which can be implanted in the body of a human or animal patient in order to compensate for organ dysfunction.

These medical devices include, in particular, artificial urinary sphincters, which comprise an inflatable occlusive cuff suitable for being arranged around a natural conduit such as the urethra or the bladder neck, a fluid reservoir in fluid connection with the cuff, and an actuator suitable for transferring the fluid between the cuff and the reservoir according to the compression to be exerted by the cuff on the natural conduit.

Such medical devices are designed to operate in a given range of fluid pressure imposed, for example, by a regulation.

However, there may be situations in which the pressure moves outside of this range.

It is therefore desirable, even in these situations, to prevent any dysfunction of the patient and to avoid any risk for the patient which could result in such a dysfunction.

SUMMARY OF THE INVENTION

An object of the invention is therefore to prevent a malfunction of the actuator which could pose a risk for the patient in the case where the patient wearing such a medical device is at a high altitude for a certain period.

Another object of the invention is to prevent a malfunction of the actuator in the case where the patient wearing the medical device is below sea level, for example when practising diving.

To this effect, the invention proposes a medical device comprising:

- a sealed casing, containing a gas, suitable for being implanted in a body of a human or animal patient,
- an inflatable element, suitable for being implanted in the body of the patient, outside of the casing,
- a fluid circuit comprising a fluid reservoir having a variable fluid volume and arranged inside the casing with a tube ensuring a fluidic connection between said reservoir and said inflatable element,
- an actuator arranged inside the casing and mechanically coupled to the fluid reservoir in order to selectively vary the volume of fluid in said reservoir,
- a control unit configured to control the actuator so as to transfer the fluid between the reservoir and the inflatable element,

- at least one sensor suitable for measuring an absolute pressure of the fluid in the fluid circuit, a force exerted on the reservoir, a gas pressure inside the casing, an atmospheric pressure or a value relating to an altitude of the patient,
- said control unit being further configured so as to:
- on the basis of a measurement from said sensor while the actuator is inactive, detect a differential between a value relating to an altitude of the patient and a reference value and
- as a function of said differential, determine a control to be issued to the actuator so as to control the pressure of fluid in the fluid circuit.

According to the advantageous, but optional, features of the invention, optionally combined:

- the control unit is configured in order, if the value relating to the altitude of the patient is greater than the first reference value, to control the actuator to reduce the volume of fluid in the inflatable element;
- the control unit is further configured to maintain said reduced volume of fluid in the inflatable element as long as the value relating to the altitude of the patient is greater than the first reference value, or the value relating to the altitude of the patient is between the first reference value and a second reference value that is less than the first reference value;
- the control unit is configured in order, if the value relating to the altitude of the patient is less than the second reference value, to determine a control for the actuator in order to increase the volume of fluid in the inflatable element;
- the control unit is configured in order, if the patient is submerged and the value relating to the altitude of the patient is less than a third reference value, to control the actuator to reduce the volume of fluid in the inflatable element;
- the control unit is further configured to maintain said reduced volume of fluid in the inflatable element, as long as the patient is submerged and the value relating to the altitude of the patient is less than the third reference value, or the value relating to the altitude of the patient is between the third reference value and a fourth reference value greater than the third reference;
- the control unit is configured in order, if the patient is submerged and the value relating to the altitude of the patient is greater than the fourth reference value, to determine a control for the actuator in order to increase the volume of fluid in the inflatable element;
- the control unit is configured to trigger the control of the actuator after the expiry of a determined period during which the value relating to the altitude of the patient is greater than the first reference value or, if the patient is submerged, the value relating to the altitude of the patient is less than a third reference;
- the fluid reservoir comprises a stationary portion and a movable portion and the actuator is mechanically coupled to said movable portion so as to linearly move said movable portion relative to the stationary portion in order to vary the volume of the reservoir;
- said at least one sensor comprises a sensor arranged in the casing, mechanically connected to the actuator and/or to the movable portion of the reservoir, arranged so as to measure a tensile and/or compressive force in the direction of movement of the movable portion of the reservoir, said measured force resulting at least from:
- the force exerted by the movable portion of the reservoir linked to the pressure in the fluid circuit, and the force exerted on the movable portion of the reservoir linked to the pressure of gas in the casing, the control unit being configured to measure the fluid pressure in the fluid circuit on the basis of said measured force;

said at least one sensor comprises a gas pressure sensor in the casing;

said at least one sensor comprises an altimeter arranged in the casing and configured to measure a value relating to the altitude of the patient;

the device further comprises a control device (remote control) outside the body of the patient and suitable for being carried by the patient, said control device comprising an atmospheric pressure sensor and being suitable for communicating, to the control unit, the pressure measured by said atmospheric pressure sensor in order to determine a value relating to the altitude of the patient;

the control unit is configured to detect the altitude differential on the basis of measurement data of said force sensor, pressure sensor, or the altimeter;

the control unit is configured to detect the altitude differential on the basis of measurement data from a first sensor among said force sensor, pressure sensor and the altimeter and to confirm said detected altitude differential on the basis of measurement data from another sensor among said force sensor, pressure sensor and the altimeter;

the control unit is configured to detect said altitude differential in a discontinuous manner;

the control unit is configured to detect the altitude differential at regular intervals of between 1 and 300 minutes, preferably between 5 and 60 minutes, more preferably between and 15 minutes;

the inflatable element is an occlusive cuff suitable for being arranged around an anatomical conduit in order to selectively close said anatomical conduit;

said device is configured to be implanted in a human or animal body in order to selectively close by means of the cuff, an anatomical conduit chosen among at least: a urethra, a gastric conduit, a colon and a rectum.

BRIEF DESCRIPTION OF THE FIGURES

Other features and advantages of the invention will become apparent from the detailed description which follows with reference to the appended drawings in which.

DETAILED DESCRIPTION OF THE EMBODIMENTS

In the present text, "patient" shall mean a human being or an animal.

The present invention relates, in particular, to active implantable medical devices that are able to close a natural conduit, in particular for combating urinary incontinence by means of an artificial sphincter that is capable of closing a urethra (in men) or the bladder neck (in women). However, the invention also relates more generally to medical devices comprising a fluid circuit that is sensitive to pressure variations generated, in particular, by changes in altitude. These other devices may include, in particular, penile implants and restrictive gastric bands.

Figure 1:
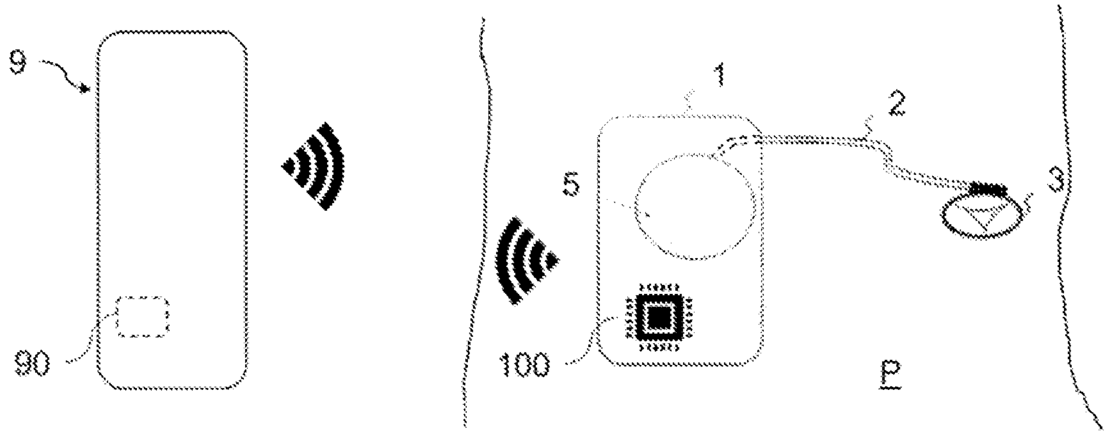
FIG. 1 shows an overview of an implantable medical device in the body of a patient and a remote control outside of the body of the patient.
Figure 2:
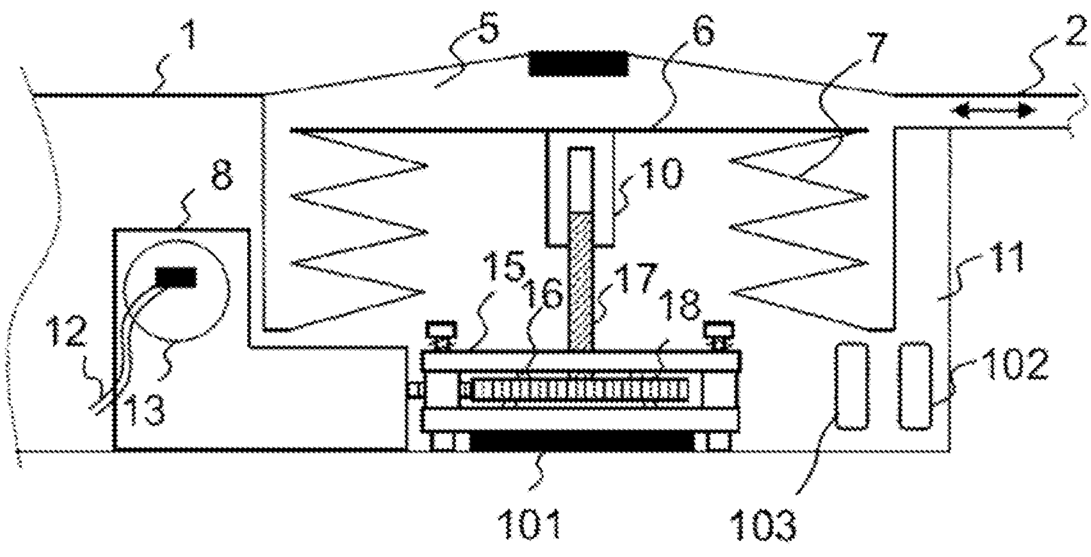
FIG. 2 is a schematic sectional view of the inside of the casing according to an embodiment.

An implantable medical device in a human or animal body is illustrated, by way of non-limiting example, in FIGS. 1 and 2.

The implantable device comprises:

a sealed casing 1 containing a gas, an inflatable element 3, outside of the casing, suitable for being implanted in the body of the patient, a fluid circuit comprising a fluid reservoir 5 having a variable fluid volume and arranged inside the casing with a tube 2 ensuring a fluidic connection between said reservoir 5 and said inflatable element 3, an actuator 8 arranged inside the casing 1 and mechanically coupled to a part of the fluid reservoir 5 in order to selectively vary the volume of fluid in said reservoir, a control unit 100 configured to control the actuator so as to transfer the fluid between the reservoir and the inflatable element.

The fluid circuit is suitable for being filled with a fluid. A variation in the volume of the reservoir 5 causes a variation in the pressure in the fluid circuit. More particularly, a reduction in the volume of the reservoir 5 leads to a transfer of fluid from the reservoir 5 to the inflatable element 3, and causes an increase in pressure in the fluid circuit. Conversely, an increase in the volume of the reservoir 5 leads to a transfer of fluid from the inflatable element 3 to the reservoir 5 and causes a reduction in pressure in the fluid circuit.

The casing, the tube and the cuff are suitable for being implanted in the body of a patient P, the contours of which are shown schematically in FIG. 1 on either side of this assembly.

Particularly advantageously, a remote control 9, outside of the body of the patient, can be used by the patient or a third-party in order to wirelessly communicate with the medical device.

Inflatable Element

The inflatable element 3 can be made of biocompatible material, such as implantable silicone, implantable polyurethane, etc. The inflatable element 3 can be made from biocompatible elastomer, for example biocompatible silicone.

The inflatable element 3 can be an inflatable occlusive cuff, in particular when the implantable system is an artificial urinary sphincter. The inflatable occlusive cuff 3 filled with fluid can be suitable for totally or partially surrounding the conduit to be closed.

Alternatively, the inflatable element 3 can be an inflatable penile implant, in particular when the implantable system is an erectile prosthesis.

Fluidic Connection

The fluidic connection 2 may consist of a tube arranged between the reservoir 5 and the inflatable element 3. A first end of the tube opens into the reservoir 5 and a second end of the tube opens into the inflatable element 3.

The fluidic connection 2 can be made of biocompatible material, such as implantable silicone, implantable polyurethane, etc. The fluidic connection 2 can be made from biocompatible elastomer, for example biocompatible silicone.

Variable Volume Reservoir

The reservoir 5 comprises a portion that is stationary relative to the casing and a portion movable relative to the stationary portion, said movable portion being movable by the actuator.

The reservoir 5 further comprises an orifice for transferring fluid from and to the exterior of the reservoir 5 to the cuff 3 via the fluidic connection 2.

According to an advantageous but non-limiting embodiment, the stationary portion of the reservoir comprises a part of the interior wall of the casing 1, and the movable portion comprises a movable wall 6 that is preferably rigid and a deformable bellows 7 extending between the movable wall 6 and the stationary portion of the reservoir.

Actuator

The actuator 8 may be suitable for controlling a linear movement of the movable wall 6, the bellows 7 being suitable for extending or compressing according to said linear movement of the movable wall 6 controlled by the actuator 8.

The actuator 8 can be chosen from any electromechanical system that can transform electrical energy into a mechanical movement with the output required to enable the movement with a force and at a required speed of the movable wall 6 of the variable volume reservoir 5. The actuator 8 can be, in particular, a piezoelectric actuator, an electromagnetic actuator which may comprise an electromagnetic motor with or without brushes, coupled or not to a reduction gear, an electroactive polymer or a shape-memory alloy.

The movable wall 6 can be moved in translation along a longitudinal axis, by the action of a drive screw 17 integral with the movable wall 6. The movable wall 6 is coupled to the drive screw 17 via a nut 10 that is integral with the movable wall 6 and having an internal thread cooperating with the thread of the screw 17. The drive screw 17 can extend substantially along the longitudinal axis. A position of the drive screw 17 may correspond substantially to a centre of the movable wall 6.

The actuator 8 is suitable for driving the drive screw 17 in rotation, for example by rotating a pinion. A rotation of the drive screw 17 around the longitudinal axis drives a movement of the movable wall 6 along the longitudinal axis, the bellows 7 compressing or extending along the longitudinal axis as a consequence.

The actuator 8 may comprise a motor 13 coupled to a reduction gear. A connector 12 makes it possible to supply power to the motor 13 according to an operating order of the motor.

The reduction gear is coupled to a toothed wheel 18 which is itself coupled to the drive screw 17, so as to transmit the torque and rotation of the shaft of the motor 13 to the drive screw 17. The drive system thus comprises a nut coupled to the drive screw and rotatable on a double acting thruster ball bearing about an axis of the screw under the effects of a drive action by the actuator 8, the nut being coupled to the screw such that a rotation of the nut drives the screw uniquely in translation in the direction of movement of the movable portion.

The rotation of the screw 17 then drives the nut in translation, which has the effect of moving the movable wall 6 in translation in a direction parallel to the axis of the screw, in other words in the direction of the longitudinal axis. The direction of movement of the movable wall 6 depends on the direction of rotation of the motor 13.

The toothed wheel 18 is housed in a block 15 by means of ball bearings 16 which allow its rotation in the block 15.

Control Unit

The implantable system can comprise a control unit 100 configured to receive a pressure setpoint in the fluid circuit, and to determine a reservoir volume 5 corresponding to the received pressure setpoint.

The control unit can also be suitable for controlling the actuator 8 so as to move the movable wall 6 of the reservoir 5 to a position corresponding to the determined volume. More particularly, in the example illustrated in FIG. 2, the control unit is suitable for emitting an order to operate the motor of the electromagnetic actuator 8 in one direction or the other, according to whether an increase or a reduction in volume of the reservoir 5 is required.

Casing

The variable volume reservoir 5 and the actuator 8 are incorporated in a sealed biocompatible casing 1 intended to be implanted in the body of the patient. The control unit 100 (not shown in FIG. 2) can also be incorporated in the casing 1. The casing also encloses an energy source (not illustrated), for example a primary or secondary battery suitable for electrically powering the control unit, the actuator and the other components of the device requiring electrical power.

The casing 1, in particular the internal volume 11 of the casing 1 surrounding the reservoir 5, contains a gas, for example an inert gas.

The casing 1 can be made of titanium. Titanium being an airtight and biocompatible material, it can be used to protect elements arranged in the casing 1, in particular electronic components such as the control unit, potential sensors, etc., from the external environment.

The casing 1 is sealed to avoid any transfer of fluid or gas from or to the intracorporeal environment.

Set

A set may comprise an implantable device, such as described above, and a remote control suitable to be used by an individual, for example by an individual in which the system is implanted.

The implantable system and the remote control comprise communication means suitable for communicating between them. The remote control can be suitable for controlling a movement of the movable portion of the reservoir by the actuator 8, in particular on the basis of a command transmitted by the communication means of the remote control to the communication means of the implantable device.

The communication means of the implantable device can be incorporated in the casing 1.

Sensors

The casing 1 can enclose one or more sensors 101, 102 and/or 103 suitable for measuring a quantity linked to the altitude at which the patient in which the medical device is implanted is located.

In certain embodiments, the casing can comprise a sensor 101 in mechanical connection with the actuator 8 and/or the movable wall 6 of the variable volume reservoir 5. Said sensor is suitable for measuring a compressive and/or tensile force in the direction of movement of the movable portion of the reservoir 5, and may consist of a sensor based on a strain gauge, or a pressure sensor coupled to a mechanism for measuring a force. When the actuator is inactive (the volume of fluid being constant in the reservoir), a variation in the force measured by the sensor translates to a variation of the fluid pressure in the fluid circuit.

In certain embodiments, an absolute pressure sensor 102, which takes into account the gas pressure inside the casing of the device and the atmospheric pressure, can be arranged inside the casing 1 and outside of the reservoir.

In certain embodiments, an atmospheric pressure sensor 90 can be arranged inside the remote control 9 external to the body of the patient.

In other embodiments, an altimeter 103 is included in the casing 1.

In all cases, the measurement data from these sensors (force, absolute pressure and atmospheric pressure sensors, altimeter) can be related to the altitude of the patient. For example, the measurement of the pressure difference between the gas pressure inside the casing and the fluid pressure in the reservoir, which is subject to the variation in atmospheric pressure, when the actuator is inactive, makes it possible to determine an altitude value for the patient.

The measurement data from each sensor are transmitted to the control unit which processes them and compares them with reference values in order to determine whether or not it is necessary to reduce the volume of fluid in the inflatable element. For reasons of legibility of the figures, the connections between the sensors and the control unit have not been illustrated. These connections can be wired or wireless.

The embodiments described above can be combined so as to take advantage of the measurement data from different sensors, for example in order to determine as robustly as possible the altitude of the patient.

Hence, for example, the control unit can determine an altitude value on the basis of measurement data from the pressure sensor 102 and/or the force sensor 101 incorporated in the casing 1 and then confirm the determined altitude on the basis of measurement data from the atmospheric pressure sensor 90 of the remote control 9 disposed outside of the body of the patient.

Alternatively, the control unit can determine an altitude value on the basis of measurements of the atmospheric pressure by the sensor 90 of the remote control 9 outside of the patient, then confirm the determined altitude on the basis of measurement data from the pressure sensor 102 and/or the force sensor 101 incorporated in the casing.

When the control unit determines a differential between the value relating to the altitude and a reference value, it can activate the medical device in order to adjust the pressure in the fluid circuit. Hence, if the value relating to the altitude is such that a risk is incurred for the operation of the medical device because of a high pressure in the fluid circuit, the control unit can activate the actuator in order to open the inflatable element, transferring fluid from the inflatable element to the reservoir, and deactivating the actuator until the altitude value has returned to a value considered acceptable for the operation of the device.

In order to avoid inappropriate deactivation of the medical device (for example if the patient is in reality not at the detected altitude, or the duration during which said patient remains at this altitude is brief), the control unit can be configured to confirm the determined attitude by means of a first sensor through measurement data from a second sensor, as explained above. Alternatively or in addition, the control unit can wait for a period of time during which the determined altitude is maintained, for example a few minutes, before commanding a reduction in the volume of fluid in the inflatable element.

Preferably, the measurements carried out by the sensors and the processing carried out by the control unit are not performed continuously, but at regular intervals in order not to consume too much power. These intervals may be, for example, between 1 and 300 minutes, preferably between 5 and 60 minutes, and more preferably between 5 and 15 minutes.

Case of the Patient Rising in Altitude

When the patient rises in altitude, for example during a journey in the mountains or on-board an aircraft, the atmospheric pressure drops.

Above an altitude of order 3000 metres, the fluid pressure in the fluid circuit is likely to become too high to allow the actuator to move the movable portion of the variable volume reservoir and therefore to open the inflatable element.

In order to avoid such a situation, when the control unit detects that the patient is at an altitude greater than a first reference value (denoted A1 in the graph of FIG. 3), the control unit controls the actuator to open the inflatable element by increasing the volume of the reservoir.

Figure 3:
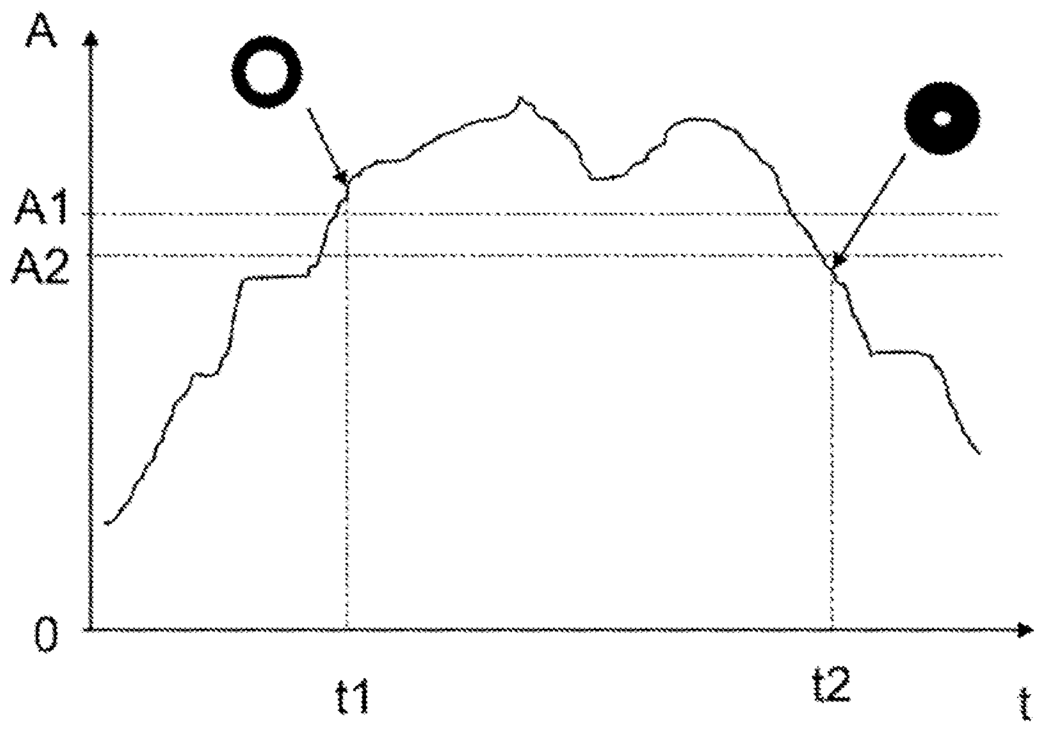
FIG. 3 is a graph schematically illustrating reference values taken into account for controlling the medical device when the patient rises up in altitude.

FIG. 3 is a graph schematically illustrating reference values taken into account for controlling the medical device when the altitude A of the patient varies over time t.

When the patient rises above the altitude A1, the control unit activates the actuator, at a time t1 which is concomitant with the passage to altitude A1 or which follows that by a few moments (for example, a few minutes), so as to increase the volume of the reservoir in order to open (i.e. at least partially deflate) the inflatable element.

While the patient remains at an altitude greater than A1, the actuator is deactivated so as to keep the inflatable element open (deflated).

A second reference value A2 advantageously defines an altitude on the basis of which the control unit can optionally reactivate the actuator in order to transfer fluid into the inflatable element.

The value A2 is advantageously chosen to be less than A1 in order to avoid a situation in which, if the patient remains for a certain period at an altitude fluctuating about A1, the control unit activates and deactivates the actuator multiple times during a relatively short period of time.

When the patient descends to the altitude A2, the control unit can activate, at a time t2 which is concomitant with the passage to altitude A2 or follows it by a few moments (for example, a few minutes) the actuator, so as to reduce the volume of the reservoir in order to at least partially inflate the inflatable element.

In other embodiments, it can be envisaged that the control unit deactivates the actuator until the patient visits a doctor who alone will be authorised to reactivate the actuator for normal operation of the medical device.

Case of a Submerged Patient

When the patient is submerged below sea level or another expanse of water, he is subject to a pressure which increases on the order of 1 bar for every 10 metres of depth. For reasons of consistency with the preceding description, the depth is considered as a negative altitude below sea-level or below the expanse of water considered. An altitude will therefore always be referred to, said altitude being lower the greater the depth of submersion.

In this situation, the medical device could be damaged by an overpressure in the fluid circuit.

Figure 4:
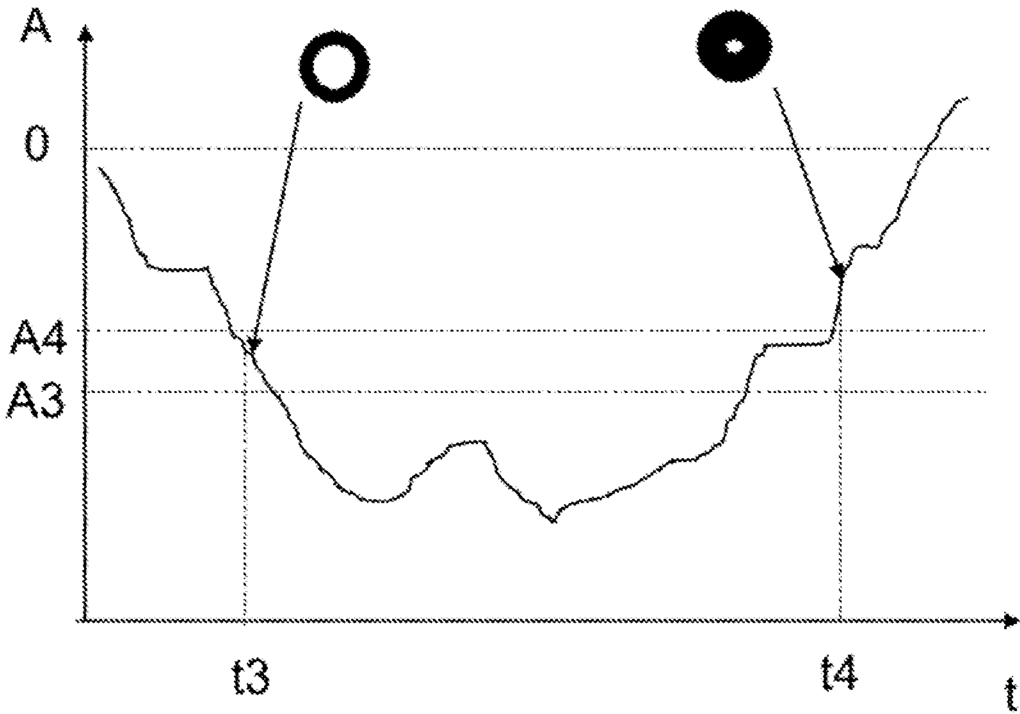
FIG. 4 is a graph schematically illustrating reference values taken into account for controlling the medical device when the patient is submerged.

FIG. 4 is a graph schematically illustrating reference values taken into account for controlling the medical device when the altitude A of the submerged patient varies over time t.

When the patient descends below the altitude A3, the control unit activates the actuator, at a time t3 which is concomitant with the passage to altitude A3 or follows it by a few moments (for example, a few minutes), so as to increase the volume of the reservoir in order to open (i.e. at least partially deflate) the inflatable element.

While the patient remains at an altitude lower than A3, the actuator is deactivated so as to keep the inflatable element open (deflated).

A second reference value A4 advantageously defines an altitude on the basis of which the control unit can optionally reactivate the actuator in order to transfer fluid into the inflatable element.

The value A4 is advantageously chosen to be greater than A3 in order to avoid a situation in which, if the patient remains for a certain period at an altitude fluctuating about A3, the control unit activates and deactivates the actuator multiple times during a relatively short period of time.

When the patient rises back to the altitude A4, the control unit can activate the actuator, at a time t4 which is concomitant with the passage to altitude A4 or follows it by a few moments (for example, a few minutes), so as to reduce the volume of the reservoir in order to at least partially inflate the inflatable element.

In other embodiments, it can be envisaged that the control unit deactivates the actuator until the patient visits a doctor who alone will be authorised to reactivate the actuator for normal operation of the medical device.

The invention claimed is:

1. A medical device comprising:

a sealed casing, containing a gas, suitable for being implanted in a body of a human or animal patient, an inflatable element, suitable for being implanted in the body of the patient, outside of the casing, a fluid circuit comprising a fluid reservoir having a variable fluid volume and arranged inside the casing with a tube ensuring a fluid connection between said reservoir and said inflatable element, an actuator arranged inside the casing and mechanically coupled to the fluid reservoir in a manner as to selectively vary the volume of fluid in said reservoir, a control unit configured to control the actuator in a manner as to transfer the fluid between the reservoir and the inflatable element, at least one sensor suitable for measuring at least one physical quantity linked to an altitude of the patient in which the medical device is implanted, the at least one physical quantity being among: an absolute pressure of the fluid in the fluid circuit, a force exerted on the reservoir, a gas pressure inside the casing, and an atmospheric pressure, the control unit being further configured to:

on the basis of a measurement of the at least one physical quantity from said sensor while the actuator is inactive, determine a value relating to the altitude of the patient, detect a differential between the value relating to the altitude of the patient and a reference value, and as a function of said differential, determine a command to be issued to the actuator in a manner as to control the pressure of fluid in the fluid circuit.

2. The device according to claim 1, wherein the control unit is configured to, based on the value relating to the altitude of the patient being greater than a first reference value, control the actuator to reduce the volume of fluid in the inflatable element.

3. The device according to claim 2, wherein the control unit is further configured to maintain the volume of fluid in the inflatable element which has been reduced, as long as the value relating to the altitude of the patient is greater than the first reference value, or the value relating to the altitude of the patient is between the first reference value and a second reference value that is less than the first reference value.

4. The device according to claim 3, wherein the control unit is configured to, based on the value relating to the altitude of the patient being less than the second reference value, determine a command for the actuator in a manner as to increase the volume of fluid in the inflatable element.

5. The device according to claim 2, wherein the control unit is configured to trigger the control of the actuator after the expiry of a determined period during which the value relating to the altitude of the patient is greater than the first reference value.

6. The device according to claim 1, wherein the control unit is configured to, based on the patient being submerged and the value relating to the altitude of the patient being less than a third reference value, control the actuator to reduce the volume of fluid in the inflatable element.

7. The device according to claim 6, wherein the control unit is further configured to maintain the volume of fluid in the inflatable element which has been reduced, as long as the patient is submerged and the value relating to the altitude of the patient is less than the third reference value, or the value relating to the altitude of the patient is between the third reference value and a fourth reference value greater than the third reference value.

8. The device according to claim 7, wherein the control unit is configured to, based on the patient being submerged and the value relating to the altitude of the patient being greater than the fourth reference value, determine a command for the actuator in a manner as to increase the volume of fluid in the inflatable element.

9. The device according to claim 6, wherein the control unit is configured to trigger the control of the actuator after the expiry of a determined period during which the value relating to the altitude of the patient is less than the third reference value.

10. The device according to claim 1, wherein the fluid reservoir comprises a stationary portion and a movable portion and the actuator is mechanically coupled to said movable portion in a manner as to linearly move said movable portion with respect to the stationary portion in a manner as to vary the volume of the reservoir.

11. The device according to claim 10, wherein said at least one sensor comprises a sensor arranged in the casing, mechanically connected to the actuator or to the movable portion of the reservoir, arranged in a manner as to measure at least one of a tensile force and a compressive force in a direction of movement of the movable portion of the reservoir, said measured force resulting at least from:

a force exerted by the movable portion of the reservoir linked to the pressure in the fluid circuit, and a force exerted on the movable portion of the reservoir linked to the pressure of gas in the casing, the control unit being configured to measure the fluid pressure in the fluid circuit on the basis of said measured force.

12. The device according to claim 11, further comprising at least one of (i) a force sensor in the casing, (ii) an altimeter in the casing, and (iii) an atmospheric pressure sensor in a control device outside the body of the patient, wherein the control unit is configured to detect the altitude differential on the basis of the measurement data of said force sensor, atmospheric pressure sensor or the altimeter.

13. The device according to claim 12, wherein the control unit is configured to detect the altitude differential on the basis of measurement data from one sensor chosen among said force sensor, pressure sensor and the altimeter and to confirm said detected altitude differential on the basis of measurement data from another sensor among said force sensor, pressure sensor and the altimeter.

14. The device according to claim 1, wherein said at least one sensor comprises a gas pressure sensor in the casing.

15. The device according to claim 1, wherein said at least one sensor comprises an altimeter arranged in the casing and configured to measure the value relating to the altitude of the patient.

16. The device according to claim 1, further comprising a control device outside the body of the patient and suitable for being carried by the patient, said control device comprising an atmospheric pressure sensor and being suitable for communicating, to the control unit, the pressure measured by said atmospheric pressure sensor in a manner as to determine the value relating to the altitude of the patient.

17. The device according to claim 1, wherein the control unit is configured to detect said altitude differential in a discontinuous manner.

18. The device according to claim 17, wherein the control unit is configured to detect the altitude differential at regular intervals of between 1 and 300 minutes.

19. The device according to claim 1, wherein the inflatable element is an occlusive cuff suitable for being arranged around an anatomical conduit in a manner as to selectively close said anatomical conduit.

20. The device according to claim 19, said device being configured to be implanted in the body of the human or animal patient in a manner as to selectively close by means of the cuff the anatomical conduit chosen among at least: a urethra, a gastric conduit, a colon and a rectum.

21. A medical device comprising:

a sealed casing, containing a gas, suitable for being implanted in a body of a human or animal patient, an inflatable element, suitable for being implanted in the body of the patient, outside of the casing, a fluid circuit comprising a fluid reservoir having a variable fluid volume and arranged inside the casing with a tube ensuring a fluid connection between said reservoir and said inflatable element, an actuator arranged inside the casing and mechanically coupled to the fluid reservoir in a manner as to selectively vary the volume of fluid in said reservoir, a control unit configured to control the actuator in a manner as to transfer the fluid between the reservoir and the inflatable element, and a control device arranged outside the body of the patient and suitable for being carried by the patient, the control device comprising an atmospheric pressure sensor and being suitable for communicating, to the control unit, an atmospheric pressure measured by the atmospheric pressure sensor;

the control unit being further configured to:

on the basis of a measurement of the atmospheric pressure from said atmospheric pressure sensor while the actuator is inactive, determine a value relating to the altitude of the patient, detect a differential between the value relating to the altitude of the patient and a reference value, and as a function of said differential, determine a command to be issued to the actuator in a manner as to control the pressure of fluid in the fluid circuit.

* * * * *